(12) United States Patent
Cohen

(10) Patent No.: US 7,201,884 B2
(45) Date of Patent: Apr. 10, 2007

(54) PROCESS AND APPARATUS FOR PERFORMING A GAS-SPARGED REACTION

(75) Inventor: Jeffrey David Cohen, Kennett Square, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 461 days.

(21) Appl. No.: 10/325,336

(22) Filed: Dec. 20, 2002

(65) Prior Publication Data

US 2003/0175186 A1   Sep. 18, 2003

Related U.S. Application Data

(60) Provisional application No. 60/344,269, filed on Dec. 26, 2001.

(51) Int. Cl.
*B01J 19/24* (2006.01)
*B01F 11/00* (2006.01)
*C12M 1/00* (2006.01)

(52) U.S. Cl. .............. 422/231; 422/224; 366/279; 366/102; 366/264; 366/304; 366/270; 261/36.1; 435/289.1; 435/295.1

(58) Field of Classification Search .............. 366/279, 366/102, 264, 304, 270; 435/289.1, 295.1; 261/36.1; 422/209, 224, 231
See application file for complete search history.

(56) References Cited

U.S. PATENT DOCUMENTS

| | | | |
|---|---|---|---|
| 3,028,314 A | 4/1962 | Means et al. | |
| 3,594,277 A | 7/1971 | Mako | |
| 3,844,897 A | 10/1974 | Mueller | |
| 4,101,384 A * | 7/1978 | Faust et al. | 435/298.1 |
| 4,108,385 A * | 8/1978 | Funk | 241/46.04 |
| 4,749,771 A | 6/1988 | Bollenrath et al. | |
| 4,900,480 A * | 2/1990 | Litz et al. | 261/36.1 |
| 5,013,665 A | 5/1991 | Suzuki et al. | |
| 5,151,368 A * | 9/1992 | Brimhall et al. | 435/286.7 |
| 5,344,766 A | 9/1994 | Ramachandran et al. | |
| 5,803,601 A * | 9/1998 | Dean | 366/270 |
| 5,972,661 A * | 10/1999 | Kubera et al. | 435/104 |
| 6,079,864 A * | 6/2000 | Dean | 366/101 |
| 6,464,384 B2 * | 10/2002 | Kubera et al. | 366/102 |
| 6,966,983 B1 * | 11/2005 | McWhirter et al. | 210/150 |
| 2002/0144598 A1 | 10/2002 | Stacy et al. | |
| 2004/0062143 A1 * | 4/2004 | Weetman | 366/279 |

FOREIGN PATENT DOCUMENTS

CH    685 631    10/1978

(Continued)

OTHER PUBLICATIONS

International Search Report dated Nov. 17, 2003.

(Continued)

*Primary Examiner*—N. Bhat

(57) ABSTRACT

An improved process, such as a microbiological or enzymatic process, and apparatus, such as an apparatus for producing a cellular product, comprising introducing a gaseous feed stream of at least one gas of low solubility into an aqueous medium containing a microorganism capable of converting said gaseous feed stream to a cellular product, entraining the gas in the aqueous medium, stirring the gas-entrained aqueous medium so that the gas is retained within the reactor for a time sufficient for the microorganism to convert the majority of the gas to product.

24 Claims, 8 Drawing Sheets

FOREIGN PATENT DOCUMENTS

| | | |
|---|---|---|
| DE | 2 322 296 | 11/1974 |
| DK | 170824 | 1/1996 |
| EP | 0185407 | 1/1990 |
| EP | 0418187 | 12/1994 |
| FR | 1438895 | 5/1965 |
| FR | 2 507 500 | 6/1981 |
| FR | 143895 | 7/1981 |
| GB | 1 296 818 | 9/1969 |
| GB | 1 206 886 | 9/1970 |
| GB | 1 453 660 | 10/1973 |
| GB | 1 472 008 | 12/1973 |
| WO | WO 00/18948 | 4/2000 |
| WO | WO 02/18617 | 3/2002 |

OTHER PUBLICATIONS

B.K. Soni, et al., "Effect of Temperature and Pressure on Growth and Methane Utilization by Several Methanotrophic Cultures", Applied Biochemistry and Biotechnology, (1998) vol. 70-72, pp. 738.

\* cited by examiner

PROCESS AND APPARATUS FOR PERFORMING A GAS-SPARGED REACTION

This application claims the benefit of U.S. Provisional Application No. 60/344,269, filed Dec. 26, 2001, which is incorporated as a part hereof for all purposes.

BACKGROUND OF THE INVENTION

An enormous abundance of byproduct natural gas results during the process of crude oil recovery. Since natural gas is predominantly methane and methane has about twenty times the greenhouse gas potential of carbon dioxide, much of it is flared near the wellhead. Flaring, however, is becoming increasingly environmentally unacceptable.

Methane is a very low-grade fuel that requires significant infrastructure to transport. Transport by high pressure pipeline or the liquefaction, storage and transport of Liquefied Natural Gas (LNG), requires pumps, pipeline, and tanks, and is too costly unless a large quantity of natural gas is available at a single location. As a result of the infrastructure cost, less than 16% of natural gas is traded internationally.

Many bio-processes using microorganisms in submerged cultures (i.e. growing in aqueous media) require oxygen for cell growth and for the conversion of reactant to a cellular product. Bio-processes traditionally use glucose (sugar) as a carbon source. For certain bio-processes methane may be used as the carbon source. Since both oxygen and methane have a low solubility in water, the absorption of gasses into the liquid must occur at a high rate to meet the biological demand of the microorganisms for both oxygen and methane.

Gas sparged bio-reactors have historically been vertical cylindrical tanks having a tank height to tank diameter aspect ratio of 3 to 5. FIG. 1 shows a perspective view of a prior art vertical tank apparatus. Bio-reactor designers have relied on this geometry to minimize plant floor space, to provide higher hydrostatic head for increased gas solubility, and to facilitate exit gas disengagement from the liquid. Solid or liquid carbon sources, traditionally glucose, have high solubility in water. Gaseous carbon sources such as methane and other hydrocarbon gases, however, have low solubility in water and present a challenge to the reactor designer.

When a gaseous hydrocarbon (e.g. methane) is used as the carbon source, a significant fraction of the gaseous hydrocarbon escapes from the liquid medium before it can be consumed by the microorganisms. Typically only as little as thirty percent of the gaseous hydrocarbon is consumed. Oxygen and oxygen enriched air are also relatively insoluble in water. A high percentage of the oxygen also escapes without being consumed. Since carbon dioxide is typically produced by the microorganisms, the effluent gas is a mixture of unconsumed gaseous hydrocarbon, oxygen (or air) and carbon dioxide. It is often both economically and environmentally unacceptable to release unused gaseous hydrocarbon into the atmosphere. Recycle of the gas mixture requires that a gas separator be employed to remove the carbon dioxide, thereby increasing the investment and the operating cost of the process.

Most prior art vertical cylindrical bio-reactors are typically stirred or agitated. In such agitated bio-reactors a gas mixture, such as methane and oxygen, is typically sparged (i.e., bubbled) at the bottom of the reactor. As the gas rises it moves through stirred regions where mechanical agitation finely divides large gas bubbles into smaller ones. This mechanical agitation also serves to thin the liquid boundary layer which surrounds the bubbles, believed to be the major resistance to gas absorption. As the buoyant force moves the gas up, and ultimately out of the liquid, the residence time of the bubble in the liquid limits the amount of gas that each bubble may deliver to the liquid. In such a reactor, the exiting gas still has a significant unconsumed portion of the initial oxygen and methane remaining, typically mixed with gaseous byproducts of the reacted material, such as carbon dioxide. This gas mixture may be recovered, the desired reagent gases being separated from the carbon dioxide and recycled back into the reactor as is taught by U.S. Pat. No. 5,344,766. Such recovery and separation increases the investment and the operating cost of the process.

Loop reactors have also been employed for carrying out microbiological processes. Such reactors are exemplified by DK 170,824, EP 185,407 and EP 418,187. Vertical loop reactors have a long up-flow tube, a long down-flow tube, and two horizontal connecting tubes between the up-flow and down-flow tubes. Such reactors circulate the liquid medium around the loop using a pump. EP 185,407 introduces the gas into the liquid medium at or near the bottom of the up-flow tube and mixes the gas and liquid using one or more static mixers. The unused gas is collected in a separator at the top of the loop, and the liquid is circulated around the loop into the down-flow tube. EP 418,187 introduces the gas into the liquid medium at one or more locations in the down-flow tube (to provide longer gas residence time) and mixes the gas and liquid with static mixers in both the down-flow and the up-flow tubes.

Horizontally oriented stirred cylindrical reactors are also known. Typical is FR 1,438,895, which discloses an air-sparged apparatus for treating wastewater. The cylindrical vessel has an orifice in the form of a slit located at the top of the vessel, parallel to its longitudinal axis. The orifice is filled with water to a height of 0.1 to 0.15 vessel diameters above the top of the vessel. The advantage provided, according to FR 1,438,895, is that the bubbles of air or gas containing oxygen are retained along at least one and preferably several revolutions in the waste waters and injected oxygen is therefore utilized with a significantly better yield than prior art devices. Since the orifice is open to the air along its top face, the vessel cannot retain gas that reaches this orifice. Such a system would be environmentally unacceptable for use in a bio-process using a gaseous hydrocarbon. Another example of a horizontally stirred reactor is U.S. Pat. No. 4,101,384. This patent utilizes a motor driven perforated paddle wheel stirring device to mix the nutrient and gas to maintain a phase state with a relative density of less that 0.3 of that of water. Another example of a horizontally stirred reactor is U.S. Pat. No. 5,151,368, which teaches the rotation of the entire reactor vessel.

A reactor design to efficiently deliver a hydrocarbon such as methane to bacteria to sequester the carbon as biomass is believed to be both environmentally and economically advantageous. Such biomass may be used as animal feed or converted to higher value materials. It is believed that a reactor that eliminates the need for gas recovery, gas separation, and gas recycling would overcome the disadvantage of the prior art.

SUMMARY OF THE INVENTION

One embodiment of this invention is a mixing apparatus for reacting a gas in a liquid medium including (a) a substantially cylindrical vessel having a substantially horizontal axis and containing the liquid medium, (b) an inlet port at a first axial end of the vessel for introducing a feed gas into the vessel, (c) an outlet port at a second axial end of the vessel for removing an effluent gas from the vessel, (d) a plurality of sequential mixing zones spaced along the axis of the vessel in each of which zones the feed gas is mixed with the liquid medium.

A further embodiment of this invention is, in a substantially cylindrical vessel having a substantially horizontal axis and containing a liquid medium, a process for reacting a feed gas with the liquid medium, involving (a) introducing the feed gas into the vessel, and (b) defining within the vessel a plurality of sequential mixing zones spaced along the axis of the vessel in each of which zones the feed gas is mixed with the liquid medium.

The present invention also provides an improved process, such as a microbiological or enzymatic process for producing a cellular product. The process involves, for example, introducing a gaseous feed stream of at least one gas of low solubility into an aqueous medium containing a microorganism capable of converting said gaseous feed stream to a cellular product. The microorganism, in such case, thereby produces a liquid phase containing the cellular product and a gaseous phase containing non-absorbed gaseous feed stream and a gaseous byproduct. The process further involves feeding said gaseous feed stream to said reactor vessel and entraining the gas in the aqueous medium, stirring the gas-entrained aqueous medium so that the gas is retained within the reactor for a time sufficient for the microorganism to convert the majority of the gas to product. The gaseous byproduct is then removed from the reactor.

In particular the invention is directed to a microbiological or enzymatic process for producing a product selected from the group consisting of proteins, carotenoids (e.g. beta-carotene, astaxanthin), and aroma chemicals (e.g. menthol, geraniol, linalool, limonene).

The present invention also provides a reaction apparatus for producing a product by introducing at least one feed gas of low solubility in an aqueous medium in the presence of a microorganism capable of converting said at least one feed gas to product, the apparatus including: a generally cylindrical vessel having an axis, the axis being substantially horizontal, an inlet port at a first axial end of the cylindrical vessel for introducing the at least one feed gas to the vessel, an outlet port at a second axial end of the cylindrical vessel for removing effluent gas from the vessel, a stirring assembly rotatable about the axis, comprising a shaft, a plurality of impeller assemblies mounted in a spaced arrangement along the shaft, each impeller assembly comprising a group of impellers arranged around the shaft, and drive means for rotating the shaft, the impellers being arranged to define a plurality of mixing zones along the axis, so that when the feed gas is introduced to the vessel through the inlet port and effluent gas is removed at the outlet port the feed gas is substantially retained within each mixing zone until displaced by the incoming feed gas, so that the feed gas is retained within the reactor until the majority of the feed gas has been converted to product.

The present invention further provides a reaction apparatus for producing a product by introducing at least one feed gas of low solubility in an aqueous medium in the presence of a microorganism capable of converting said at least one feed gas to product, the apparatus including a generally cylindrical vessel having a longitudinal axis, a first axial end wall, a second axial end wall, and a longitudinal wall having a generally circular cross-section, the axis being substantially horizontal, an inlet port positioned substantially at the bottom of the cylindrical vessel near the first axial end for introducing the at least one feed gas to the vessel, an outlet port positioned substantially at the top of the cylindrical vessel at the second axial end of the cylindrical vessel for removing effluent gas from the vessel, a plurality of stirring assemblies, each comprising a shaft extending through the longitudinal wall of the vessel the shaft being positioned along a chord of the circular cross-section, an impeller assembly mounted on a first end of the shaft, each impeller assembly comprising a hub supporting a group of inclined blades arranged around the shaft, and drive means at a second end for rotating the shaft, the impellers being arranged to define a plurality of mixing zones along the axis, so that when the feed gas is introduced to the vessel through the inlet port and effluent gas is removed at the outlet port the feed gas is substantially retained within each mixing zone until displaced by the incoming feed gas, so that the feed gas is retained within the reactor until the majority of the feed gas has been converted to product.

DETAILED DESCRIPTION OF THE INVENTION

The present invention provides a horizontally-oriented, vented, gas-sparged reactor, such as a bio-reactor, enabling the majority of the feed gas to be fully absorbed in the aqueous medium without breakthrough into the exit gas stream. In the case of a biological reaction, the invention enables costly or environmentally sensitive gas feedstocks to be sequestered as biomass or bio-transformed to product rather than being released in the vented exit gas. The horizontally oriented, gas-sparged reactor of the present invention is typically closed, and has the following benefits over the prior art:

1) The gas-holdup [dispersed gas/(dispersed gas+liquid volume)] is independent of the gas-sparging rate;
2) A gas-liquid dispersion is created using an economical stirring power per stirred volume ratio;
3) The dispersed gas residence time may range from near zero to essentially infinite time;

4) High gas-dispersion residence times enable nearly full depletion/absorption of gas reagent from the gas feed stream prior to exiting the reactor; and 5) Gas moves from the reactor inlet to the outlet in essentially a plug flow.

Figure 1:
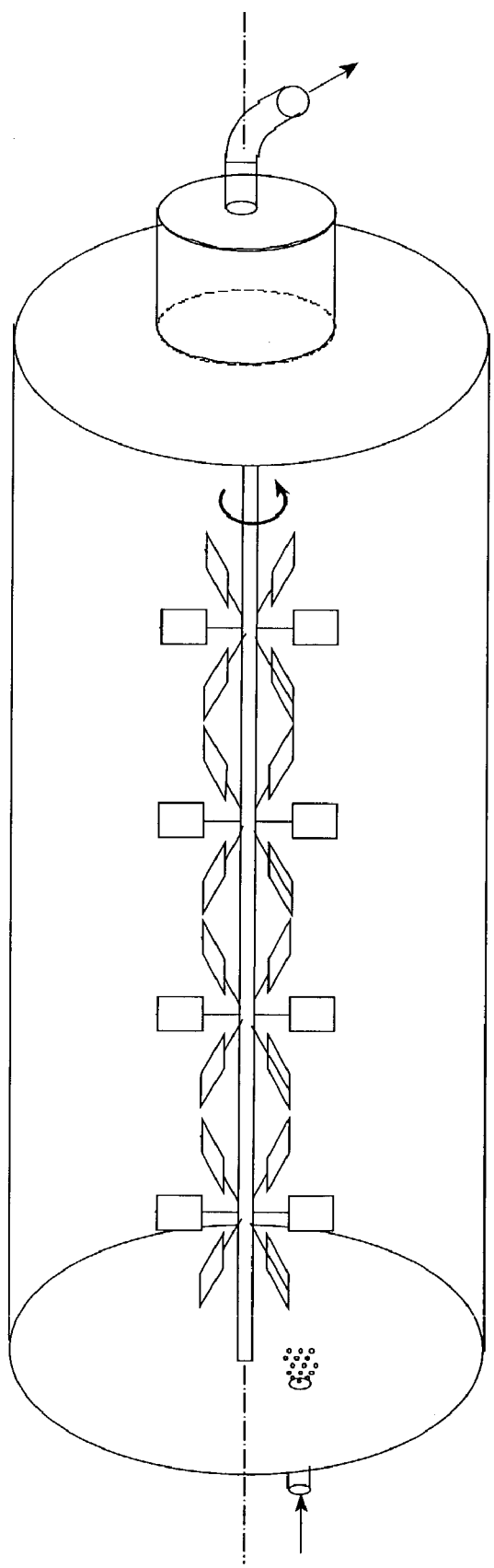
FIG. 1 shows a sectional view of a prior art vertical cylinder apparatus.
Figure 2:
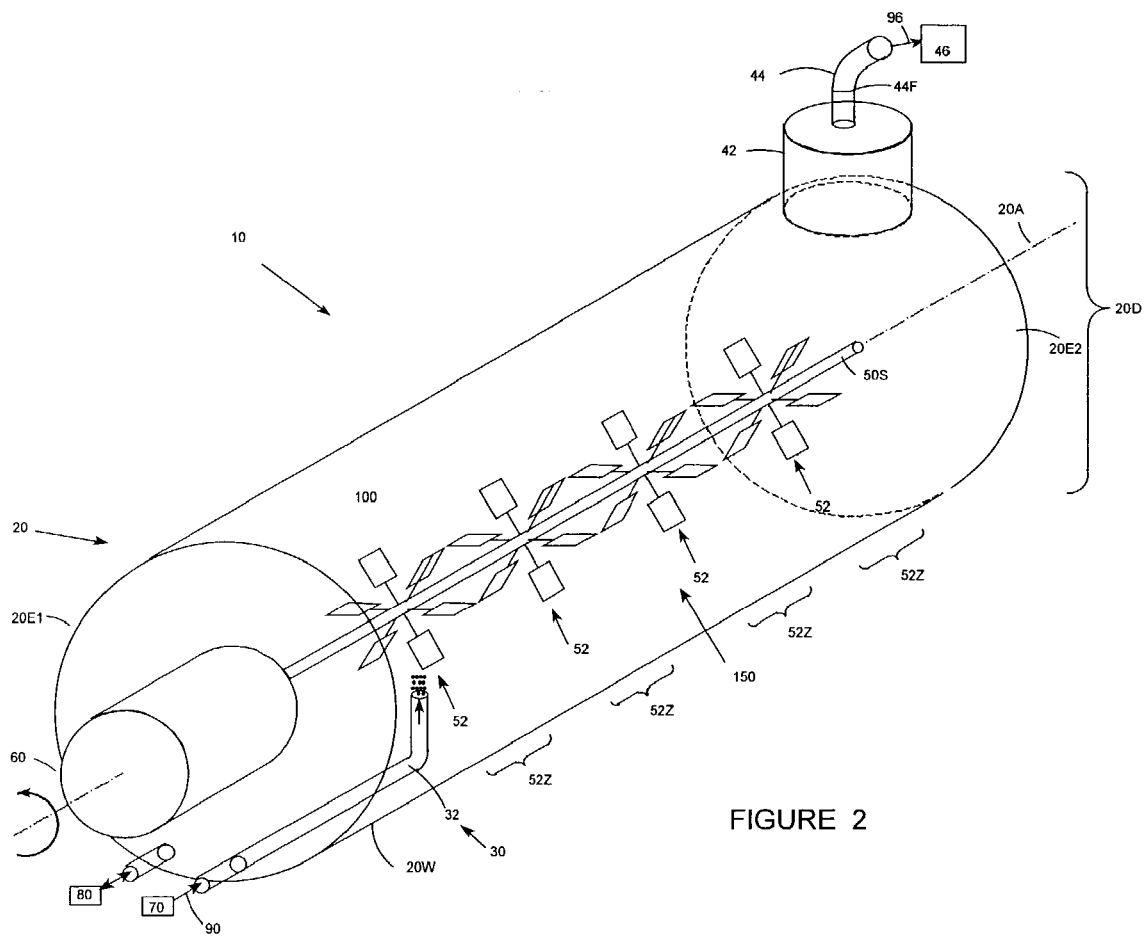
FIG. 2 is a perspective view of a first embodiment a reactor apparatus, showing a horizontal shaft stirring assembly.

FIG. 2 is a perspective view of a first embodiment of a reactor apparatus, with the reactor vessel shown as transparent for clarity of illustration. The reactor apparatus 10 includes a cylindrical or substantially cylindrical vessel 20 containing a liquid medium 100, a stirring assembly 50, a drive means 60 for rotating the stirring assembly 50, a gas supply 70, a liquid medium removal/replenishment system 80. The cross section of the reactor vessel may be shaped in the form a circle, such as a perfect circle, or may be other shapes that are not a perfect circle but are rather substantially circular. The cylindrical vessel 20 has a first end wall 20E1 and a second end wall 20E2, a generally cylindrical longitudinal wall 20W having a longitudinal axis 20A and a diameter dimension 20D, a feed gas inlet 30 adjacent the first end wall 20E1 and an effluent gas outlet 40 adjacent the second end wall 20E2. The longitudinal axis 20A is horizontal or substantially horizontal, as shown, or may be inclined from the horizontal at an angle up to about ten degrees, with the first end wall 201 higher than the second end wall 20E2. The cylindrical vessel 20 may be constructed of any suitable material that is compatible with the liquid medium 100, such as stainless steel, steel with a suitable inner liner or even glass.

The feed gas inlet 30 comprises one or more pipes 32, which are used to introduce a gas mixture 90 into the liquid medium 100 containing a reactant, such as a microorganism, 102 adjacent to the first end wall 20E1. The effluent gas outlet 40 comprises a chamber 42 for collecting the effluent gas 96, a filter 44F and an outlet pipe 44 for transporting the effluent gas 96 to a gas analyzer 46 and then to suitable disposal means (not shown). The stirring assembly 50 comprises a longitudinal shaft 50S and a plurality of impeller assemblies 52 spaced along the shaft.

Figure 3:
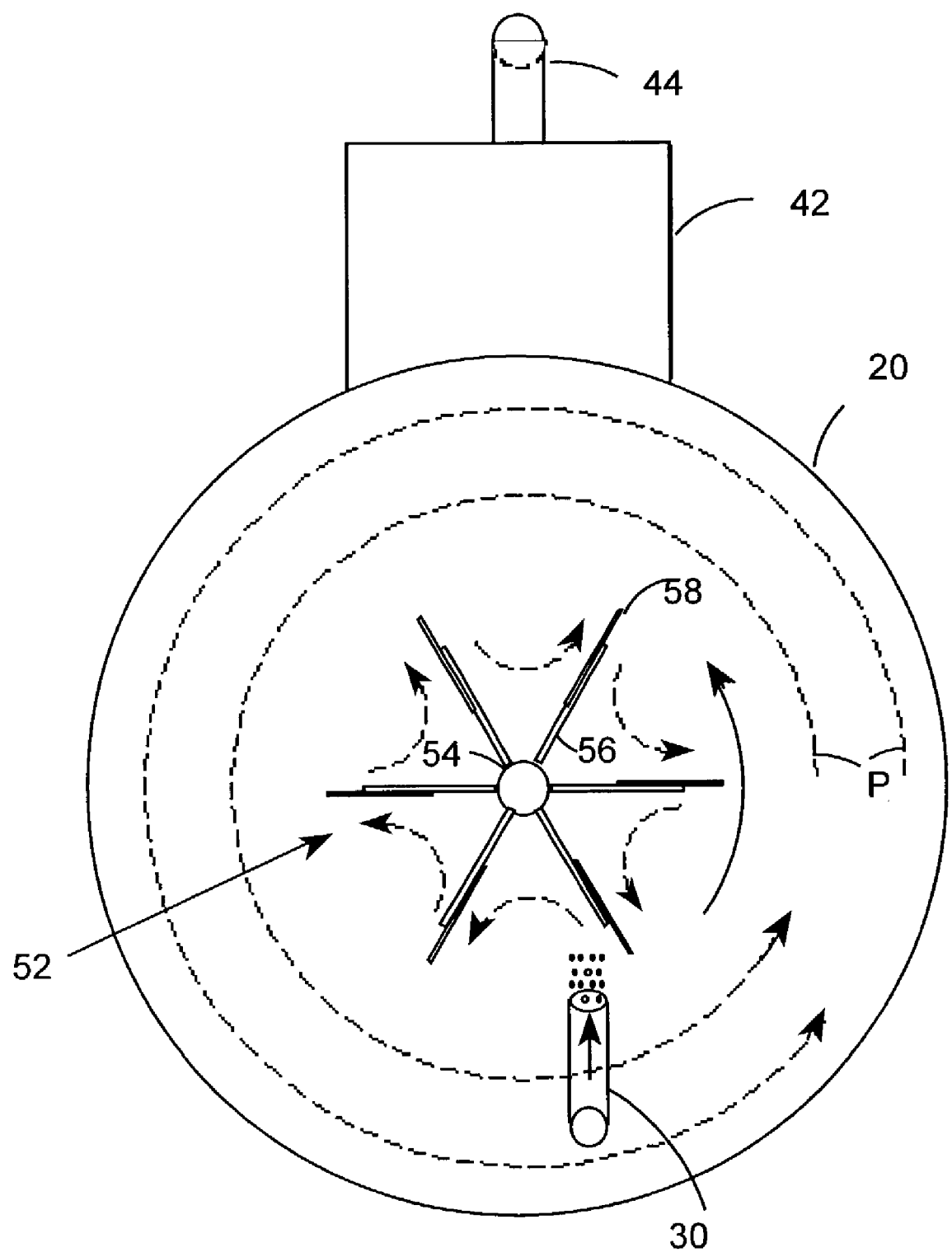
FIG. 3 is a sectional view of FIG. 2, taken along section lines 3—3, also showing the flow patterns of the gas-entrained liquid.

Referring now to FIG. 3, each impeller assembly comprises a hub 54, a group of impellers arranged around the shaft, each impeller comprising an arm 56 attached to the hub 54 holding one or more blades 58. As shown each impeller assembly 52 has six impellers, but any suitable number may be employed. The overall diameter of each impeller assembly 52 is typically from about 0.3 to about 0.45 the vessel diameter 20D. When rotated by drive means 60, the stirring assembly 50 causes the feed gas 90 to become entrained as small bubbles in the liquid medium 100 and to travel around the generally circular cross section of the vessel 20. The drive means may comprise any suitable conventional drive means, such as an electric motor, a motor and gearbox, or a hydraulic motor.

The speed of the impeller assemblies is such that the tip speed of the blades 58 is less than about 300 meters per minute, in keeping with generally accepted practice for microorganisms contained in liquid media. Typical power levels of about 4.5 watts per liter of liquid media have been found to be adequate. When rotated, each impeller assembly 52 establishes a mixing zone in the immediate vicinity of the impeller and imparts a radial motion to the mixture of the liquid medium and feed gas. The entrained gas bubbles follow a generally radial flow path P as shown in the sectional view of FIG. 3 and tend to remain in the mixing zone until they are displaced by incoming bubbles of gas. Gas bubbles displaced from the first mixing zone tend to remain in the second mixing zone until a sufficient number have accumulated to displace gas bubbles into the third mixing zone. This displacement process continues until the gas mixture arrives at the effluent gas collection chamber 42.

By controlling the rate of feed gas 90 introduction, the residence time of the feed gas in the reactor can be controlled. When, for example, the reactor is first started in a biological reaction, reactor 10 is first filled with a growth medium and sterilized to remove undesirable microorganisms, then the reactor is inoculated with the desired microorganisms. An initial feed gas supply rate is established sufficient to supply the initial population of microorganisms. Effluent gas 96 is analyzed by the gas analyzer 46 to determine the content of the effluent gas. The gas analyzer 46 may analyze gas samples withdrawn from the effluent gas stream on either a periodic basis or continuously. The result of the gas analysis is then used to control the feed gas rate. The rate of feed of feed gas may, for example, be reduced if undesired amounts of unreacted feed gas are present in the effluent stream from the reactor. As may be appreciated, the population of microorganisms increases over time as long as proper growing conditions and a sufficient quantity of feed gas is supplied to the vessel. If the quantity of feed gas is insufficient the cells of the microorganism may undergo a process known as lysis.

In a batch operated bio-reactor the cell concentration of the microorganism steadily increases to a point where the metabolic requirements of the cells, i.e. the biological gas demand, equals the maximum oxygen transfer rate (OTR) or the maximum methane transfer rate (MTR) of the bio-reactor. Beyond this point the maintenance requirements of the cell will go unmet and the cells begin to lyse. Surface active agents such as polypeptides and polysaccharides cause the gassed, agitated growth medium to foam. This foam, composed of gas, cells, and aqueous growth medium exits the reactor and may block the outlet filter causing pressure to build in the reactor and stop the process. To prevent excessive foaming in an aerobic methanotrophic process it is necessary to meet the biological gas demand for oxygen and carbon (methane). The maximum OTR and MTR may be the system features which dictate at which cell concentration the bio-reactor operates when changing from the batch operating mode to the continuous operating mode.

When the cell concentration reaches a level that approaches the maximum OTR or MTR, part of the liquid phase containing the cellular material is typically withdrawn from the reactor and the reactor 10 is replenished with substantially the same volume of fresh growth media 100. This may be performed either periodically or continuously. By continuing to analyze the effluent gas, the feed rate of the feed gas may be adjusted to the new concentration of microorganisms. The reaction may thus be controlled in view of the rate or extent of increase in content of the desired reaction product, such as cellular material, or in view of the fact that the concentration of a byproduct gas, such as CO2, will increase in gradient fashion moving in direction from the inlet end of the vessel toward the outlet end.

Figure 4:
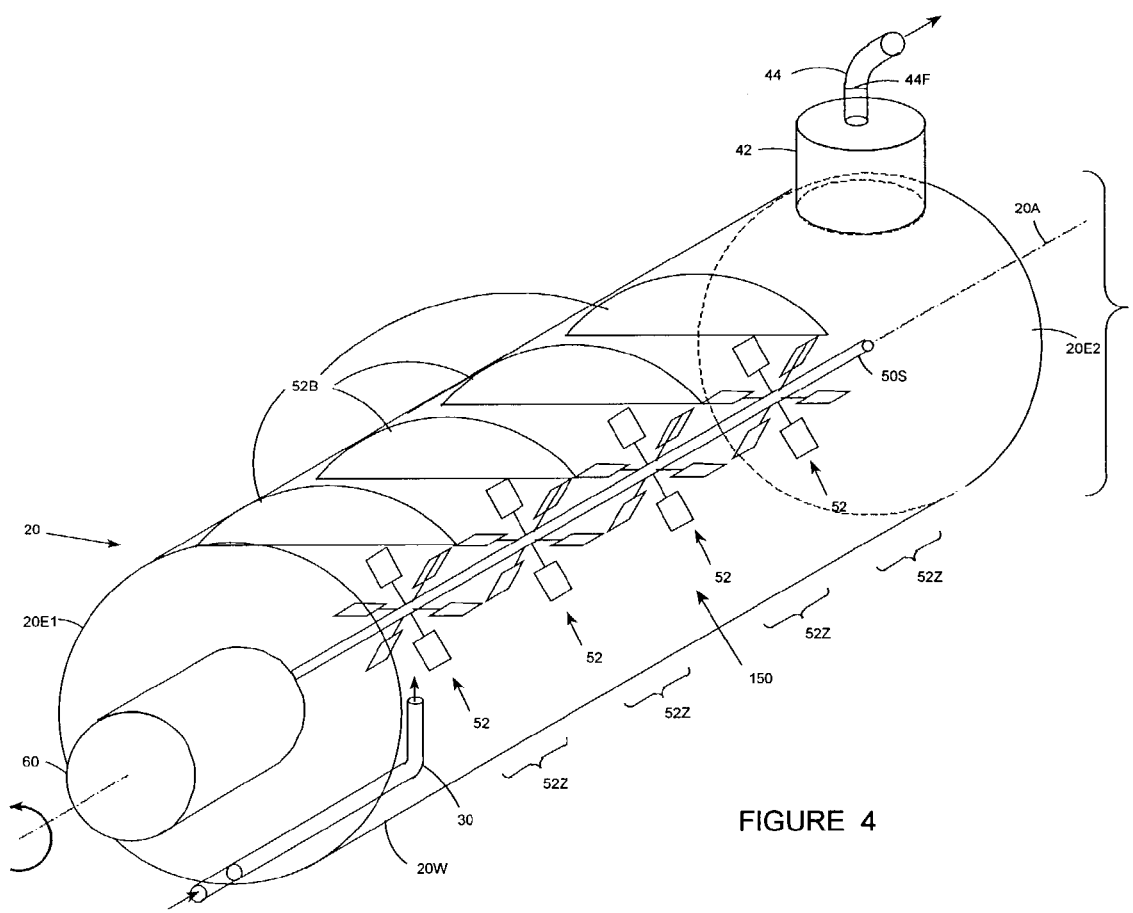
FIG. 4 is a perspective view showing mixing zone baffles.

Referring now to FIG. 4, to further enhance retention of the feed gas in each mixing zone a plurality of generally crescent shaped baffles 52B may be positioned at the top of the reactor between pairs of impeller assemblies 52. The bottom edge 52E of these baffles 52B is positioned so that the liquid level of the growth medium 100 is above the edge 52E when the stirring assembly is not being rotated.

Figure 5:
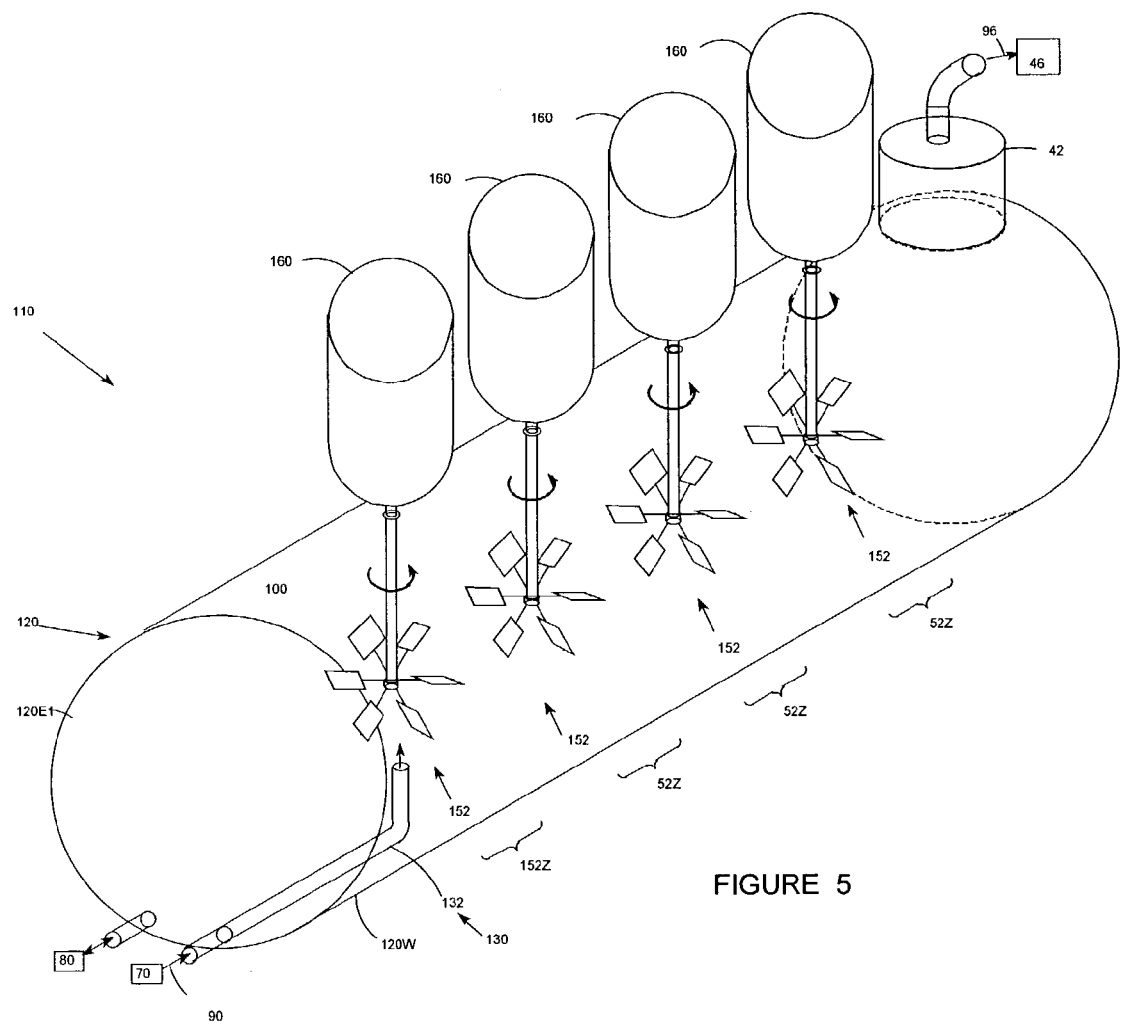
FIG. 5 is a perspective view of a second embodiment a reactor apparatus.
Figure 6:
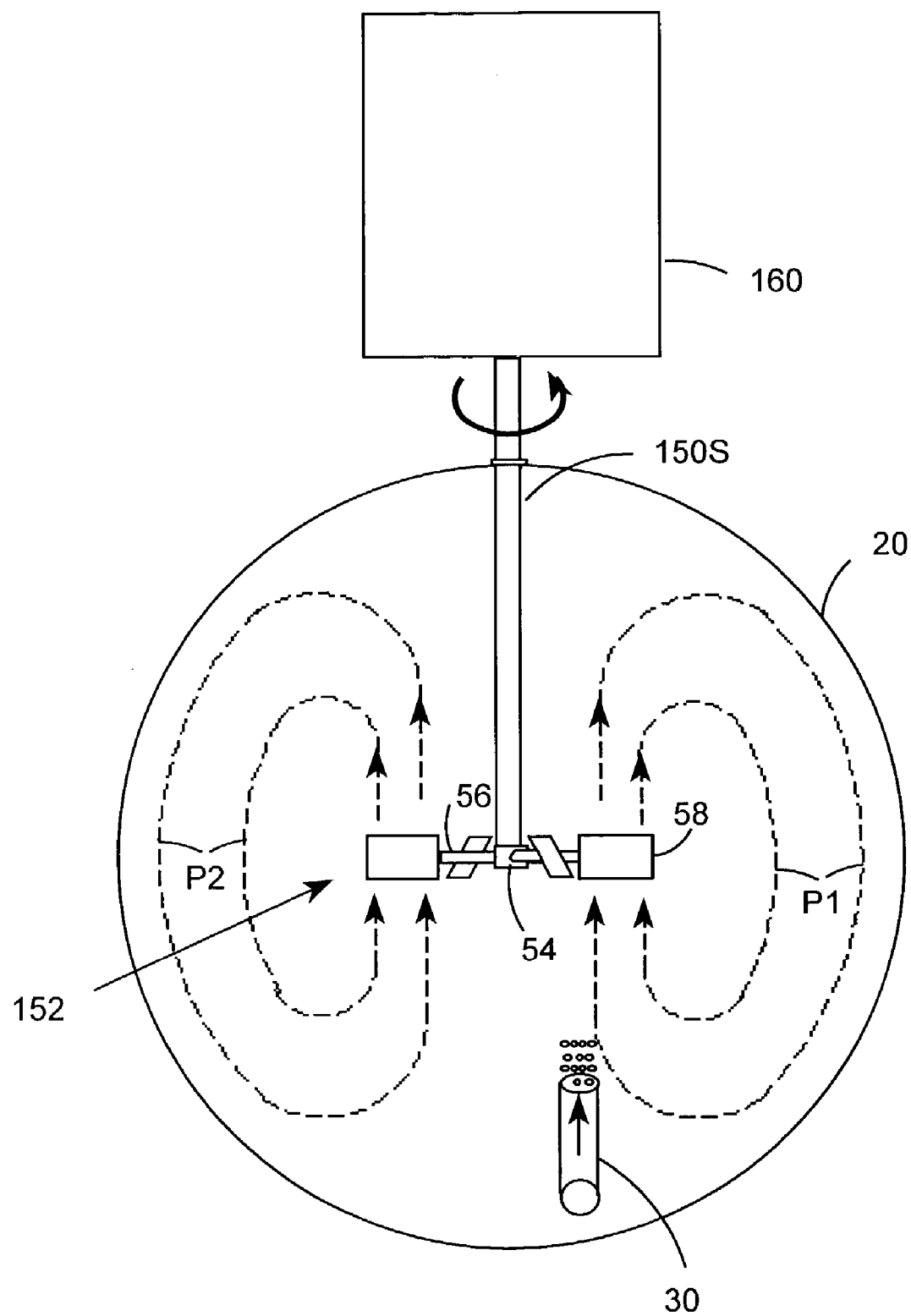
FIG. 6 is a sectional view of FIG. 5, taken along section lines 6—6, showing a first impeller arrangement where the impeller shaft is positioned along a diametrical chord of the vessel and showing the resulting flow patterns of the gas-entrained liquid.

A second embodiment of a reactor apparatus 110 is seen in FIG. 5, with the reactor vessel again shown as transparent for clarity of illustration. The reactor apparatus 110 comprises a generally cylindrical vessel 120 containing a liquid medium 100, a plurality of stirring assemblies 150 spaced along the length of the reactor vessel 120, a drive means 160 for rotating each stirring assembly 150, a gas supply 170, a liquid medium removal/replenishment system 180. The cylindrical vessel 120 has a first end wall 120E1 and a second end wall 120E2, a generally cylindrical longitudinal wall 120W having a longitudinal axis 120A and a diameter dimension 120D, a feed gas inlet 130 adjacent the first end wall 20E1 and an effluent gas outlet 140 adjacent the second end wall 20E2. Each stirring assembly 150 comprises a shaft 150S with an impeller 152 mounted at a first end of the shaft 150. In FIG. 6, each impeller assembly 152 comprises a hub 154, a group of impellers arranged around the shaft, each impeller comprising an arm 156 attached to the hub 154 holding one or more inclined blades 158. As shown each impeller assembly 152 has six impellers, but any suitable number may be employed. The overall diameter of each impeller assembly 152, from blade tip to diametrically opposed blade tip, is typically from about 0.3 to about 0.45 the vessel diameter 20D.

The stirring assembly 150 may be mounted so that the shaft 150S lies along a diametrical chord of the circular cross section of the vessel 120 (or along the longest internal dimension if the cross section is only substantially circular), as is seen in FIGS. 5 and 6. When so mounted and rotated by drive means 160, the stirring assembly 150 causes the feed gas 90 to become entrained as small bubbles in the liquid medium 100 and to travel around the generally circular cross section of the vessel 20 in two counter current paths as seen in the sectional view of FIG. 6. The entrained gas bubbles follow a generally clockwise flow path P1 as shown in the right portion or a generally counter-clockwise flow path P2 as shown in the left portion of the sectional view of FIG. 6 and tend to remain in the mixing zone until they are displaced by incoming bubbles. Gas bubbles displaced from the first mixing zone tend to remain in the second mixing zone until a sufficient number have accumulated to displace gas bubbles into the third mixing zone. This displacement process continues until gas arrives at the effluent gas collection chamber 142.

Figure 7:
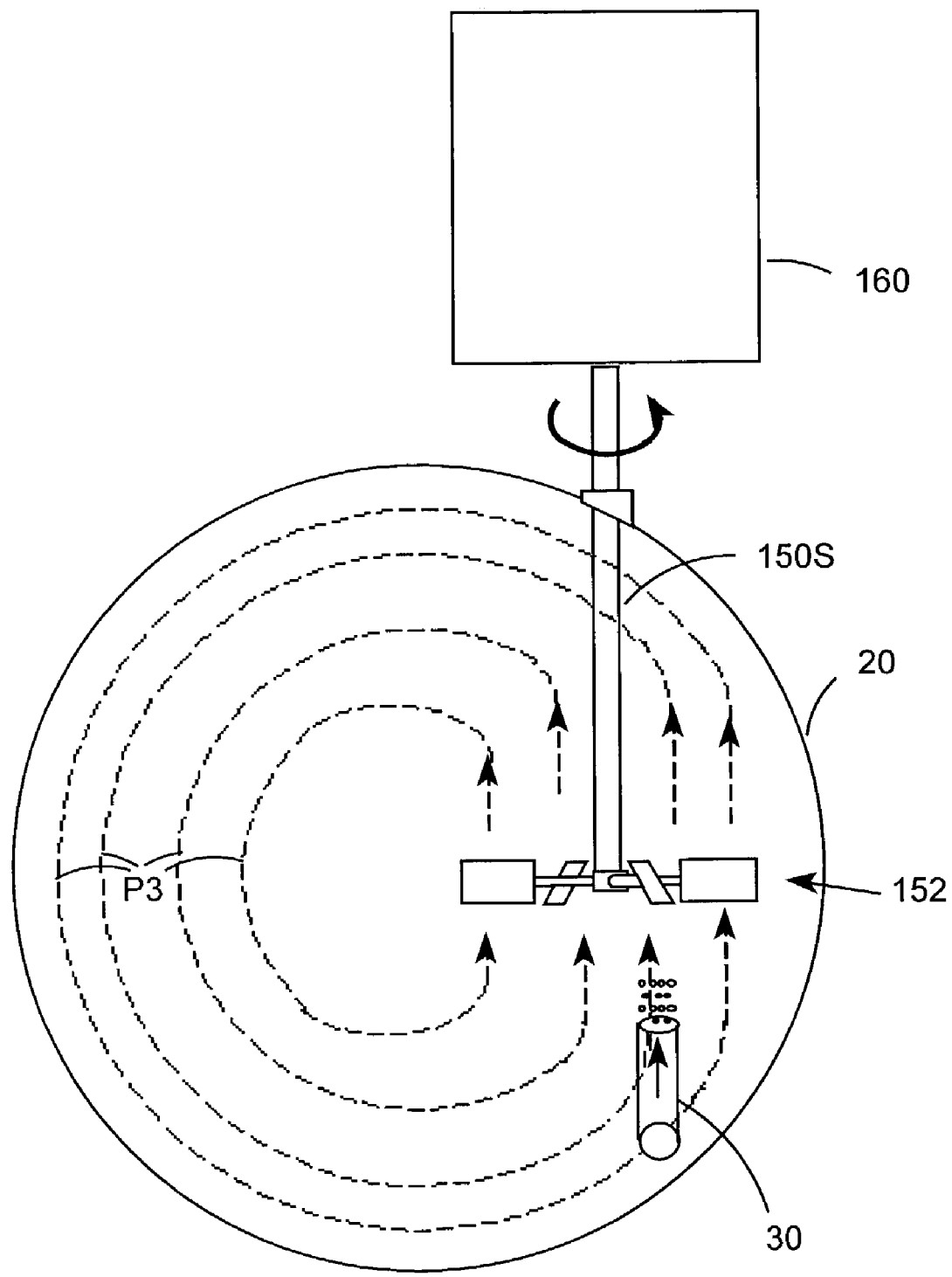
FIG. 7 is a sectional view showing a second impeller arrangement as an alternative arrangement to that of FIG. 6, where the impeller shaft is positioned along a non-diametrical chord of the vessel and showing the resulting flow patterns of the gas-entrained liquid.

Alternatively the stirring assembly 150 may be mounted so that the shaft 150S lies along a non-diametrical chord of the circular cross section of the vessel 120, as is seen in FIG. 7. When the stirring assembly 150 is so mounted and rotated by drive means 160, the stirring assembly 150 causes the feed gas 90 to become entrained as small bubbles in the liquid medium 100 and to travel around the generally circular cross section of the vessel 20 in a generally circular path P3.

By horizontally orienting the agitated bio-reactor and placing the gas inlet and outlet at opposite ends of the reactor, the residence time of the gas in the liquid may be prolonged since the buoyant force is no longer responsible for moving the gas toward the reactor's gas outlet. Indeed if the horizontal vessel is inclined with the inlet end slightly higher than the outlet end, the buoyant force can used to further extend the residence time of the gas in the liquid. By prolonging the residence time of the gas in the liquid medium a greater fraction of the gas species (e.g. oxygen, methane) may be absorbed from the bubble into the liquid and consumed by the reactant such as a microorganism. A horizontally-oriented reactor, such as a bio-reactor, may operate more efficiently than a vertically oriented reactor since gas sparging rates may be decreased and a reduced amount of feed gas (e.g. oxygen, methane) will exit from the reactor.

A mixing zone may be defined by entraining feed gas therein such as by imparting a radial motion and flow to the feed gas. Radial motion may be imparted by stirring the mixture of liquid medium and feed gas with an assembly that is rotatable about the vessel axis, and comprises a shaft and a plurality of impeller assemblies mounted in a spaced arrangement along the shaft. The impeller thrusts toward the longitudinal wall of the cylindrical vessel rather than along the direction of the longitudinal axis of the vessel. Means for entraining a feed gas in a mixing zone include a multi-bladed paddle agitator, a turbine impeller such as a Rushton impeller, or a flat bladed turbine, a backswept turbine, a Scaba SRGT, or an impeller with an open straight blade, a bladed dish or a vertical curved blade.

Gas is entrained in a mixing zone until displaced into the next succeeding zone by incoming feed gas. Aspects of the act of entraining a feed gas, and retaining an entrained gas in a mixing zone, are thus the regulation of the rate of feed of a feed gas to the vessel, and the regulation of the rate of stirring of the feed gas and the mixture of liquid medium and feed gas.

The efficiency of the reaction may be improved by utilizing a relatively large volume of liquid, for example liquid may be at least about 80 percent of the volume of the vessel, or the contents of the vessel may have a bulk density of at least about 0.8 g/L. When providing for the entrainment of gas in a liquid medium in a reactor vessel containing such a large proportion of liquid, it is often found beneficial to use a vessel that has a length to diameter ratio of at least about 4, preferable at least about 8, and more preferably at least about 10.

Various embodiments of the invention that are thus provided are, for example, in a microbiological or enzymatic process for producing a product, involving introducing a gaseous feed stream of at least one gas of low solubility into an aqueous medium containing a microorganism, the microorganism being capable of converting said gaseous feed stream to a cellular product, thereby producing a liquid phase containing said cellular product and a gaseous phase containing non-absorbed gaseous feed stream and a gaseous byproduct; further involving feeding said gaseous feed stream to said reactor vessel and entraining the gas in the aqueous medium, stirring the gas-entrained aqueous medium in a radial direction to define a plurality of sequential mixing zones, so that the gas is retained within each mixing zone within the reactor for a time sufficient for the microorganism to convert a majority of the gas to product and removing the gaseous byproduct from the reactor.

A further embodiment of the invention that is thus provided is, in a microbiological or enzymatic process for producing a product selected from the group consisting of proteins, carotenoids, and aroma chemicals, involving introducing a gaseous feed stream comprising a gas mixture of at least one gaseous hydrocarbon and an oxygen-rich gas into an aqueous medium in a reactor containing a microorganism capable of converting said gas mixture to the product, thereby producing an aqueous phase containing said product and a gaseous phase containing non-absorbed gaseous hydrocarbon, non-absorbed oxygen-rich gas and gaseous byproduct; further involving feeding said gas mixture to said reactor and entraining the gas mixture in the aqueous medium, stirring the gas-entrained aqueous medium to define a plurality of sequential mixing zones, so that the gas mixture is retained within each mixing zone within the reactor for a time sufficient for the microorganism to convert a majority of the gaseous hydrocarbon to the product and removing the gaseous byproduct from the reactor.

Yet another embodiment of the invention that is thus provided is, in a process for producing a protein comprising contacting a hydrocarbon feed stream involving a gas mixture of at least one gaseous hydrocarbon and an oxygen-rich gas in an aqueous medium in a reactor in the presence of a microorganism capable of converting said gaseous hydrocarbons to protein, thereby producing an aqueous phase containing said protein and a gaseous phase containing non-absorbed gaseous hydrocarbon, non-absorbed oxygen and carbon dioxide; further involving feeding said gaseous hydrocarbon and oxygen-rich gas to said reactor and entraining the gas mixture in the aqueous medium, stirring the gas-entrained aqueous medium to define a plurality of sequential mixing zones, so that the gas mixture is retained each mixing zone within the reactor for a time sufficient for the microorganism to convert a majority of the hydrocarbon gas to protein and removing effluent gas from the reactor.

Yet another embodiment of the invention that is thus provided is, in a reaction apparatus for producing a product by introducing at least one feed gas of low solubility in an aqueous medium in the presence of a microorganism capable of converting said at least one gas to product, the apparatus including a generally cylindrical vessel having an axis, the axis being substantially horizontal, an inlet port at a first axial end of the cylindrical vessel for introducing the at least one gas to the vessel, an outlet port at a second axial end of the cylindrical vessel for removing effluent gas from the vessel, a stirring assembly rotatable about the vessel axis, including a shaft, a plurality of impeller assemblies mounted in a spaced arrangement along the shaft, each impeller assembly comprising a group of impellers arranged around the shaft, and drive means for rotating the shaft, the impellers being arranged to define a plurality of mixing zones along the axis and for mixing the gas entrained liquid in a radial direction so that when the feed gas is introduced to the vessel through the inlet port and effluent gas is removed at the outlet port the feed gas is substantially retained within each mixing zone until displaced by the incoming feed gas, so that the feed gas is retained within the reactor until a majority of the feed gas has been converted to product.

Yet another embodiment of the invention that is thus provided is, in a reaction apparatus for producing a protein by contacting a hydrocarbon feed stream comprising a gas mixture of at least one gaseous hydrocarbon and an oxygen-rich gas in an aqueous medium in the presence of a microorganism capable of converting said gaseous hydrocarbons to protein, the apparatus including a generally cylindrical vessel having an axis therethrough, the axis being substantially horizontal, an inlet port at a first axial end of the cylindrical vessel for introducing the gas mixture to the vessel, an outlet port at a second axial end of the cylindrical vessel for removing effluent gas from the vessel, a stirring assembly rotatable about the axis, comprising a shaft, a plurality of impellers mounted on the shaft arranged as impeller assemblies along the shaft, and drive means for rotating the shaft, the impellers being arranged to define a plurality of mixing zones along the axis, so that when the gas mixture is introduced to the reactor through the inlet port and effluent gas is removed at the outlet port, the gas mixture is substantially retained within each mixing zone until displaced by incoming gas mixture, so that the gas mixture is retained within the reactor until a majority of the gaseous hydrocarbon has been converted to protein.

Yet another embodiment of the invention that is thus provided is, in a reaction apparatus for producing a product by introducing at least one feed gas of low solubility in an aqueous medium in the presence of a microorganism capable of converting said at least one gas to product, the apparatus including a generally cylindrical vessel having a longitudinal axis, a first axial end wall, a second axial end wall, and a longitudinal wall having a generally circular cross-section, the axis being substantially horizontal, an inlet port positioned substantially at the bottom of the cylindrical vessel near the first axial end for introducing the at least one gas to the vessel, an outlet port positioned substantially at the top of the cylindrical vessel at the second axial end of the cylindrical vessel for removing effluent gas from the vessel, a plurality of stirring assemblies, each comprising a shaft extending through the longitudinal wall of the vessel the shaft being positioned along a chord of the generally circular cross-section of the vessel, an impeller assembly mounted on a first end of the shaft, each impeller assembly including a hub supporting a group of inclined blades arranged around the shaft, and drive means at a second end for rotating the shaft, the impellers being arranged to define a plurality of mixing zones along the axis, so that when the feed gas is introduced to the vessel through the inlet port and effluent gas is removed at the outlet port the feed gas is substantially retained within each mixing zone until displaced by the incoming feed gas, so that the feed gas is retained within the reactor until a majority of the feed gas has been converted to product.

Yet another embodiment of the invention that is thus provided is, in an aqueous medium containing a reactant, from which both a product and a by-product are obtained in the reaction of the reactant with at least one gas, a process for reacting the reactant with a gas, involving feeding a gas to the aqueous medium, stirring the aqueous medium to entrain a gas in a plurality of sequential mixing zones, retaining within a mixing zone a gas entrained therein for a time sufficient to produce, from the reaction of the reactant with the gas, product in greater amount than by-product, and removing the by-product from the aqueous medium.

The invention may be further appreciated from the following examples, which serve to illustrate but do not limit the invention.

EXAMPLE 1

A bio-reactor having a seven-liter total volume was used to aerobically grow *Methylomonas* sp. 16a as a submerged culture using methane as the carbon source. The reactor had a cylindrical geometry having a length of 17.25 inches and a diameter of 5.25 inches, thus producing an aspect ratio of between three and four. The reactor was oriented such that the length/long dimension of the cylinder was horizontal. The reactor vessel contained four evenly spaced, wall-mounted baffles along the length dimension to prevent vortexing and promote turbulence during mechanical agitation. Agitation was provided by three Rushton turbine impellers, equally spaced within the initial three-quarter length of the reactor. Each turbine had six flat blades with an outer diameter of 2.0 inches. The mixing power was provided by a variable speed motor directly coupled to the agitator shaft having a maximum speed of 1000 revolutions per minute (rpm). Gas entered the system through a 0.25 inch outside diameter stainless steel tube open at the end. The tube opening was located in close proximity to the impeller fastened to the end of the stirring shaft. Gas exited the reactor through a chilled condenser at the opposite end of the vessel.

The working volume was approximately 5.5 liters of liquid. When filled with 5.5 liters of liquid the headspace volume above the liquid was composed of approximately 0.55 liters of gas. When a high degree of agitation was provided (e.g. shaft speed>=700 rpm) the headspace gas in the cylindrical portion of the reactor became fully dispersed in the liquid.

Temperature was measured using a 100-ohm platinum thermistor. Temperature was controlled by pumping heated or chilled water through a heat exchanger tube immersed in the reaction medium. Dissolved oxygen was measured using an Ingold-Mettler-Toledo dissolved oxygen probe. Dissolved oxygen concentration was controlled by controlling both the gas flow rate though the reactor and the stirring speed. The pH of the mixture was measured using an Ingold-Mettler-Toledo pH probe. The pH of the mixture was controlled by pumping acid or base liquids into the reactor as needed.

Seed inoculum for the bio-reaction was prepared by placing 250 milliliters of growth medium in a baffled 500 milliliter Erlenmeyer flask. A vial containing approximately 1 milliliter of frozen cell suspension was thawed and added to the flask. The flask was placed on a shaker table and agitated at 210 rpm for 36 hours. The temperature was controlled at 30 degrees C.

The 250 milliliters of seed inoculum was transferred to the bio-reactor which contained growth medium. Proportional amounts of methane and air were sparged into the reactor. The gas proportion was dictated by the microorganism's metabolism. The dissolved oxygen level was controlled by a combination of gas sparging rate and agitator speed. During the course of the batch process samples of cell suspension were withdrawn from the reactor to measure cell density both by spectrophotometry and by cell isolation by centrifugation followed by drying and weighing. The batch process operated for 30 hours and the maximum cell optical density measured 12.1 at 550 nanometers (nm) wavelength.

Applicants made the following biological deposits under the terms of the Budapest Treaty on the International Recognition of the Deposit of Micro-organisms for the Purposes of Patent Procedure:

| Depositor Identification Reference | International Depository Designation | Date of Deposit |
|---|---|---|
| *Methylomonas* 16a | ATCC PTA 2402 | Aug. 21, 2000 |

EXAMPLE 2

A 1.5 milliliter vial of frozen *Methylomonas* sp. 16a cell suspension was thawed and placed into a 500 milliliter baffled Erlenmeyer flask, which contained 250 milliliters of inoculum growth medium and 1.0 milliliter of methanol. The flask was capped with a Morton Closure, which permitted the diffusion of gas in and out of the flask. The inoculum growth medium was composed of:

Inoculum Growth Medium

| Ingredient | Quantity (grams/liter) |
|---|---|
| NaNO3 | 0.85 |
| KH2PO4 | 0.5 |
| MgCl2.6H2O | 0.2 |
| CaCl2.2H2O | 0.1 |
| 1M Hepes buffer pH 7 | 50 milliliters |
| Solution 1 | 10 milliliters |

Solution 1

| Ingredient | Quantity (grams) |
|---|---|
| nitrilotriacetic acid | 12.8 |
| FeCl2.4H2O | 0.3 |
| CuCl2.2H2O | 0.0254 |
| MnCl2.4H2O | 0.1 |
| CoCl2.6H2O | 0.312 |
| ZnCl2 | 0.1 |
| H3BO3 | 0.01 |
| Na2MoO4.2H2O | 0.01 |
| NiCl2.6H2O | 0.184 |
| Deionized water | 1000 |

The flask was placed onto a shaker table set at 30 degrees C. and moving at 210 rpm. The flask contents were incubated for 27 hours producing the reactor inoculum E98010-90-2. The final optical density measured 0.653 at 550 nm.

The bio-reactor used was described in Example 1. The reactor growth medium used was composed of:

Reactor Growth Medium

| Ingredient | Quantity (grams/liter) |
|---|---|
| KH2PO4 | 0.5 |
| MgCl2.6H2O | 0.2 |
| CaCl2.2H2O | 0.1 |
| 1 M Hepes buffer pH 7 | 50 |
| Solution 1 | 10 |

5.25 Liters of Reactor Growth Medium were placed into the reactor. The pH probe was calibrated. The reactor was steam sterilized at 121 degrees C. for 40 minutes then cooled and maintained at 30 degrees C. 1.0 milliliter of Mazu DF-204 antifoam available from BASF Corporation was added to the reactor. After more than 6 hours of polarization the dissolved oxygen probe was calibrated. Air and methane were sparged to the reactor, each controlled at 0.06 standard liters per minute (SLPM). The reactor agitator speed was clamped to a lower limit of 360 rpm. The dissolved oxygen controller was set to 5% of air saturation using agitator speed to maintain the set-point. The pH was controlled at 7.0 with the addition of H2SO4 or NH4OH as needed. The NH4OH was used for pH control as well as a nitrogen source.

Approximately 250 milliliters of the inoculum was added to the reactor. The cell suspension was sampled occasionally and measured for optical density (O.D.).

A BTZ Growth Medium concentrate was then prepared containing the ingredients listed below:

Reactor Growth Medium Concentrate

| Ingredient | Quantity (grams) |
| --- | --- |
| KH2PO4 | 26.25 |
| MgCl2.6H2O | 10.5 |
| CaCl2.2H2O | 5.25 |
| Solution 1 | 525 |
| Deionized water | 475 |

The Reactor Growth Medium concentrate was filter sterilized and added to the reactor during the course of the batch bio-process.

The timecourse of the bio-process was as follows:

| Time of Day | Hours Run | stirrer speed (rpm) | methane flow (slpm) | airflow (slpm) | O.D.@550 nm |
| --- | --- | --- | --- | --- | --- |
| 10:20 | 0 | 364 | 0.06 | 0.06 | — |
| 14:00 | 2.3 | 661 | 0.06 | 0.06 | 0.374 |
| 23:46 | 13.5 | 978 | 0.06 | 0.10 | 0.820 |
| 2:05 | 15 | 990 | 0.06 | 0.18 | 1.488 |
| 5:30 | 17.2 | 990 | 0.06 | 0.38 | 3.72 |
| 7:30 | 19.2 | 990 | 0.06 | 0.41 | 5.86 |
| 9:30 | 21.2 | 990 | 0.06 | 0.42 | 7.36 |
| 11:30 | 23.2 | 989 | 0.06 | 0.42 | 8.15 |
| 13:30 | 25.2 | 990 | 0.07 | 0.47 | 9.6, 9.8 |
| 17:35 | 31.3 | 990 | 0.07 | 0.56 | 12.25 |
| 20:36 | 34.4 | 990 | 0.07 | 0.46 | 11.62 |
| 22:20 | 36.1 | 990 | 0.08 | 0.54 | 13.7 |
| 6:30 | 44.3 | 990 | 0.08 | 0.54 | 24.7, 22.2 |

EXAMPLE 3

Two hundred fifty milliliters of a viable cell suspension were prepared as detailed in Example 2. The flask was placed onto a shaker table set at 30 degrees C. and moving at 210 rpm. The flask contents were incubated for 30.5 hours producing the reactor inoculum. The final optical density measured 1.016 at 550 nm.

The bio-reactor used was as described in Example 1. An oxygen gas monitor, model Ultima(™) O2, manufactured by the Mining Safety Appliances Company, Pittsburgh, Pa. was used to measure the oxygen mole fraction in the gas exit stream of the reactor. The medium used was composed of (Solution 1 is as described in Example 2):

Reactor Growth Medium

| Ingredient | Quantity (grams/liter) |
| --- | --- |
| NH4Cl | 0.585 |
| KH2PO4 | 0.5 |
| MgCl2.6H2O | 0.2 |
| CaCl2.2H2O | 0.1 |
| 1 M Hepes buffer pH 7 | 50 |
| Solution 1 | 10 |

5.25 Liters of Reactor Growth Medium were placed into the reactor. The pH probe was calibrated. The reactor was steam sterilized at 121 C for 40 minutes then cooled and maintained at 30 C. 1.0 milliliter of BASF Mazu DF-204 antifoam was added to the reactor. After more than 6 hours of polarization the dissolved oxygen probe was calibrated.

Air and methane were sparged to the reactor, each controlled at 0.06 standard liters per minute (SLPM). The reactor agitator speed was clamped to a lower limit of 360 rpm. The dissolved oxygen controller was set to 5% of air saturation using agitator speed to maintain the set-point. The pH was controlled at 7.0 with the addition of H2SO4 or NaOH as needed.

Approximately 250 milliliters of the inoculum was added to the reactor. The cell suspension was sampled occasionally and measured for optical density.

A Reactor Growth Medium concentrate was then prepared containing the ingredients listed below (Solution 1 is as described in Example 2):

Reactor Growth Medium Concentrate

| Ingredient | Quantity (grams) |
| --- | --- |
| NH4Cl | 55.4 |
| KH2PO4 | 26.25 |
| MgCl2.6H2O | 10.5 |
| CaCl2.2H2O | 5.25 |
| Solution 1 | 525 |
| Deionized water | 475 mL. |

The Reactor Growth Medium concentrate was filter sterilized and added to the reactor during the course of the batch bio-process. The time course of the bio-process was as follows:

| Hrs Run | stirrer speed (rpm) | methane flow (slpm) | air flow (slpm) | Optical density at 550 nm | feed O2% | exit O2% | O2% absorbed |
| --- | --- | --- | --- | --- | --- | --- | --- |
| 0 | 364 | 0.06 | 0.06 | 0.0482 | 10.5 | | |
| 16.25 | 453 | 0.06 | 0.06 | 0.328 | 10.5 | 6.9 | 34.2 |
| 21.5 | 986 | 0.06 | 0.06 | | 10.5 | 1.6 | 84.8 |
| 24 | 985 | 0.06 | 0.10 | 1.65 | 13.0 | 2.2 | 83.1 |
| 26 | 986 | 0.06 | 0.14 | | 14.6 | 2.4 | 83.6 |
| 26.75 | 986 | 0.06 | 0.16 | | 15.1 | 2.7 | 82.1 |
| 27.25 | 986 | 0.06 | 0.18 | | 15.6 | 2.9 | 81.4 |
| 27.75 | 986 | 0.06 | 0.20 | | 16.0 | 3.2 | 80.0 |
| 28.5 | 986 | 0.06 | 0.22 | | 16.3 | 3.4 | 79.1 |
| 30 | 986 | 0.06 | 0.24 | 6.65 | 16.6 | 4.0 | 75.9 |

As the batch bio-process proceeded growth medium concentrate was added to the vessel. As the cell concentration increased the volumetric airflow rate increased to meet the biological oxygen demand. The percentage of O2 absorbed ranged from 34.2% to 84.8%.

EXAMPLE 4

Two hundred fifty milliliters of a viable cell suspension were prepared as detailed in Example 2. The flask was placed onto a shaker table set at 30 degrees C. and moving at 210 rpm. The flask contents were incubated for 30.5 hours producing the reactor inoculum. The final optical density measured 1.016 at 550 nm.

The bio-reactor used was as described in Example 1. An oxygen gas monitor, Ultima(™) O2, manufactured by the Mining Safety Appliances Company, Pittsburgh, Pa. was used to measure the oxygen mole fraction in the gas exit stream of the reactor. The reactor growth medium used was composed of (Solution 1 is as described in Example 2):

Reactor Growth Medium

| Ingredient | Quantity (grams/liter) |
| --- | --- |
| NH4Cl | 0.585 |
| KH2PO4 | 0.5 |
| MgCl2.6H2O | 0.2 |
| CaCl2.2H2O | 0.1 |
| 1 M Hepes buffer pH 7 | 50 |
| Solution 1 | 10 |

A volume of 5.25 liters of reactor growth medium was placed into the reactor. The pH probe was calibrated. The reactor was steam sterilized at 121 degrees C. for 40 minutes then cooled and maintained at 30 degrees C. A volume of 1.0 milliliters of BASF Mazu DF-204 antifoam was added to the reactor. After more than 6 hours of polarization the dissolved oxygen probe was calibrated. Air and methane were sparged to the reactor, each controlled at 0.06 standard liters per minute (SLPM). The reactor agitator speed was clamped to a lower limit of 360 rpm. The dissolved oxygen controller was set to 5% of air saturation using agitator speed to maintain the set-point. The pH was controlled at 7.0 with the addition of H2SO4 or NaOH as needed.

Approximately 250 milliliters of the inoculum was added to the reactor. The cell suspension was sampled occasionally and measured for optical density. A Reactor Growth Medium concentrate was then prepared containing the ingredients listed below (Solution 1 is as described in Example 2):

Reactor Growth Medium Concentrate

| Ingredient | Quantity (grams) |
| --- | --- |
| NH4Cl | 55.4 |
| KH2PO4 | 26.25 |
| MgCl2.6H2O | 10.5 |
| CaCl2.2H2O | 5.25 |
| Solution 1 | 525 |
| Deionized water | 475 |

The Reactor Growth Medium concentrate was filter sterilized and added to the reactor during the course of the batch bio-process. The time course of the bio-process was as follows:

| Hours Run | stirrer speed (rpm) | methane flow (slpm) | air flow (slpm) | O.D @550 nm | feed O2 % | exit O2 % | % O2 absorbed |
| --- | --- | --- | --- | --- | --- | --- | --- |
| 0 | 364 | 0.06 | 0.06 | 0.0482 | 10.5 | — | — |
| 16.25 | 453 | 0.06 | 0.06 | 0.328 | 10.5 | 6.9 | 34.2 |
| 21.5 | 986 | 0.06 | 0.06 | — | 10.5 | 1.6 | 84.8 |
| 24 | 985 | 0.06 | 0.10 | 1.65 | 13.0 | 2.2 | 83.1 |
| 26 | 986 | 0.06 | 0.14 | — | 14.6 | 2.4 | 83.6 |
| 26.75 | 986 | 0.06 | 0.16 | — | 15.1 | 2.7 | 82.1 |
| 27.25 | 986 | 0.06 | 0.18 | — | 15.6 | 2.9 | 81.4 |
| 27.75 | 986 | 0.06 | 0.20 | — | 16.0 | 3.2 | 80.0 |
| 28.5 | 986 | 0.06 | 0.22 | — | 16.3 | 3.4 | 79.1 |
| 30 | 986 | 0.06 | 0.24 | 6.65 | 16.6 | 4.0 | 75.9 |

As the batch bio-process proceeded growth medium concentrate was added to the vessel. As the cell concentration increased the volumetric airflow rate increased to meet the biological oxygen demand. The percentage of O2 absorbed ranged from 34.2% to 84.8%.

EXAMPLE 5

A mathematical model was written and a computer simulation was performed to simulate the effect of reactor aspect ratio on gas absorption rate and cell growth rate of *Methylomonas* sp16a. in a horizontally-oriented bio-reactor. Five unsteady-state material balances were written for the following components: gas-phase methane concentration, gas-phase oxygen concentration, dissolved methane concentration, dissolved oxygen concentration, and cell concentration. Since the cell growth rate is dependent on the dissolved methane and oxygen concentrations, the cell growth was simulated by calculating the dissolved gas concentrations through time.

At the start of each computer simulation the bio-reactor contained reactor growth medium and an initial cell concentration. The methane and air gas flow rates fed to the reactor were dependent upon the methane concentration contained in the reactor exit gas stream. A constraint embodied in the mathematical model was to increase the feed methane and air flows if the exit methane concentration remained equal to or below 10 mole percent.

Figure 8:
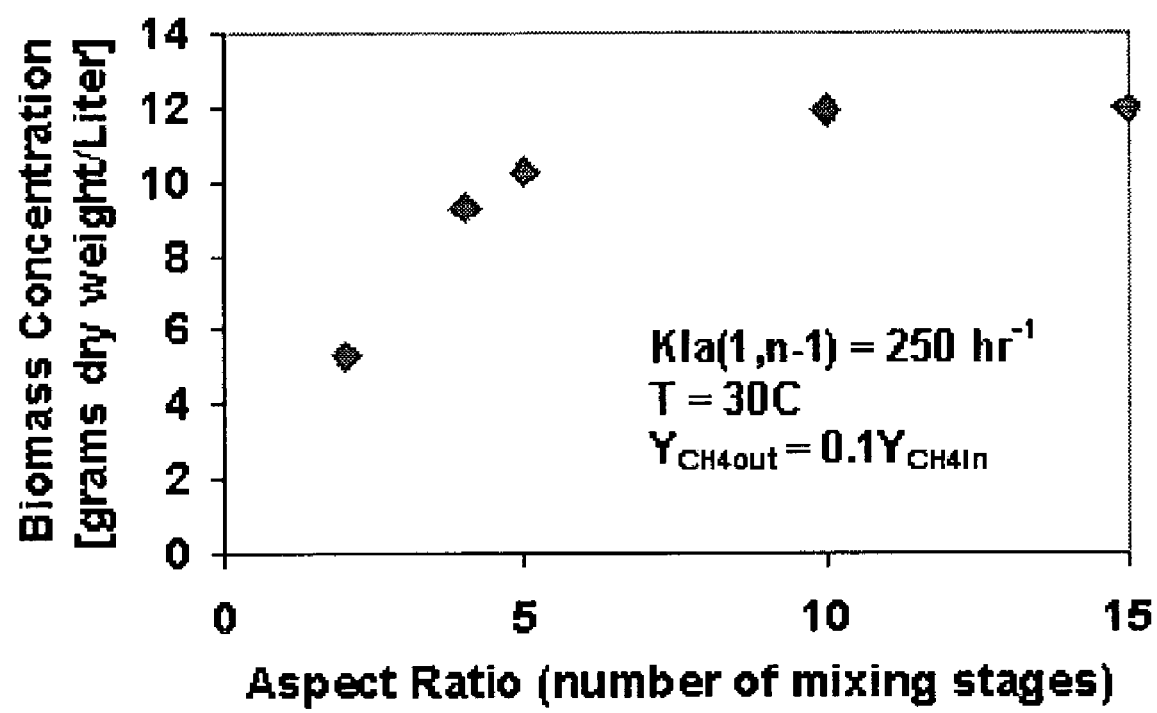
FIG. 8 is a plot showing the effect of the aspect ratio of the vessel on biomass accumulation.

Aspen Custom Modeler Version 10.1, a computer software application from Aspen Technology Incorporated, Ten Canal Park, Cambridge, Mass. 02141 U.S.A., was used to numerically integrate the unsteady-state material balances with respect to time. Several computer simulations were performed wherein the reactor aspect ratio (i.e., vessel length to diameter ratio) was varied from one (1) to fifteen (15) while keeping the reactor volume constant. These simulations revealed the effect of reactor aspect ratio on cell accumulation during a fixed period of time. FIG. 8 illustrates biomass accumulation as a function of reactor aspect ratio.

Gas Solubility

As used herein the term "low solubility" means that the solubility of the gas in the aqueous medium is less that ten (10) millimoles (mmol) per liter. Table 1A shows the solubility of oxygen in water at various temperatures at a pressure of one atmosphere. Table 1B shows the solubility of oxygen in solutions of hydrochloric acid, sulfuric acid and sodium chloride. Data is from *International Critical Tables*, Vol. III, p. 271, McGraw-Hill Book Company, New York 1928 and F. Todt, *Electrochemische Sauerstoffmessungen*, W. de Guy and Co. Berlin, 1958.

TABLE 1A

Solubility of $O_2$ of air (20.8 mole % $O_2$) in water at various temperatures at 1 Atmosphere.

| Temp deg. C. | Water $O_2$ mmol/Liter |
| --- | --- |
| 0 | 2.18 |
| 10 | 1.70 |
| 15 | 1.54 |
| 20 | 1.38 |
| 25 | 1.26 |
| 30 | 1.16 |
| 35 | 1.09 |
| 40 | 1.03 |

TABLE 1B

Solubility of O2 of air (20.8 mole %
O2) in solutions of acid or salt
O$_2$, mmol/Liter

| Electrolyte Conc. M | HCl | H$_2$SO$_4$ | NaCl |
| --- | --- | --- | --- |
| 0.0 | 1.26 | 1.26 | 1.26 |
| 0.5 | 1.21 | 1.21 | 1.07 |
| 1.0 | 1.16 | 1.12 | 0.89 |
| 2.0 | 1.12 | 1.02 | 0.71 |

TABLE 2

Grams of gas dissolved in 100 g of water when the
total pressure above the solution is 1 atmosphere.

| Gas | Solubility g per 100 g of water |
| --- | --- |
| Acetylene | 0.117 |
| Ammonia | 52.9 |
| Bromine | 14.9 |
| Carbon dioxide | 0.169 |
| Carbon monoxide | 0.0028 |
| Chlorine | 0.729 |
| Ethane | 0.0062 |
| Ethylene | 0.0149 |
| Hydrogen | 0.00016 |
| Hydrogen sulfide | 0.385 |
| Methane | 0.0023 |
| Nitrogen | 0.0019 |
| Oxygen | 0.0043 |
| Sulfur dioxide | 11.28 |

What is claimed is:

1. A mixing apparatus for reacting a gas in a liquid medium, comprising
   (a) a substantially cylindrical vessel having a substantially horizontal axis and containing the liquid medium,
   (b) an inlet port at a first axial end of the vessel for introducing a feed gas into the vessel,
   (c) an outlet port at a second axial end of the vessel for removing an effluent gas from the vessel,
   (d) a plurality of sequential mixing zones spaced along the axis of the vessel in each of which zones the feed gas is mixed with the liquid medium, and
   (e) an impeller assembly in each mixing zone that imparts a radial and circumferential motion to the feed gas, and entrains the feed gas in the mixing zone until it is displaced therefrom by incoming feed gas or by feed gas displaced from the previous mixing zone.

2. An apparatus according to claim 1 wherein the feed gas is entrained within the vessel for a time sufficient for substantially all of the feed gas to be reacted to product.

3. An apparatus according to claim 1 wherein an impeller assembly rotates on a shaft that is rotatable about the horizontal vessel axis.

4. An apparatus according to claim 1 wherein the impeller assemblies sweep a diameter of about 0.3 to 0.45 of the vessel diameter.

5. An apparatus according to claim 1 wherein the impeller assemblies are rotated at a speed such that the velocity of the outer ends of the impellers does not exceed 300 meters per minute.

6. An apparatus according to claim 1 wherein the axis of the cylindrical vessel is inclined so that the second axial end is lower than the first axial end, the inclination being at an angle of up to about ten degrees from the horizontal.

7. An apparatus according to claim 1 wherein the cylindrical vessel is tapered at a taper angle up to about ten degrees, the taper angle providing a smaller diameter of the cylinder at the second axial end.

8. An apparatus according to claim 1 wherein the cylindrical vessel has a length to diameter ratio of greater than about four.

9. An apparatus according to claim 1 wherein the cylindrical vessel has a length to diameter ratio of greater than about ten.

10. An apparatus according to claim 1 wherein the impeller assembly rotates on a shaft that extends through a longitudinal wall of the substantially cylindrical vessel and is positioned along a chord of a substantially circular cross-section of the vessel.

11. An apparatus according to claim 10 wherein the shaft is positioned along a diametrical chord of the cross-section of the vessel.

12. An apparatus according to claim 10 wherein the shaft is positioned along a non-diametrical chord of the cross-section of the vessel.

13. An apparatus according to claim 1, 3 or 10 which comprises one or more baffles.

14. An apparatus according to claim 13 wherein one or more baffles is crescent-shaped, and (a) has a lower edge positioned above the shaft and between the impeller assemblies, and (b) is of a height such that the lower edge of the baffle is immersed in the liquid medium.

15. An apparatus according to claim 1 wherein liquid comprises at least about 80 percent of the volume of the vessel.

16. An apparatus according to claim 1 that further comprises a regulator that controls the rate of introduction of feed gas into the vessel.

17. An apparatus according to claim 16 that further comprises an analyzer that determines the content of the effluent gas.

18. An apparatus according to claim 1 that further comprises an analyzer that determines the content of the effluent gas.

19. An apparatus according to claim 18 wherein the gas analyzer determines the content of the effluent gas on a periodic or continuous basis.

20. An apparatus according to claim 18 wherein the gas analyzer determines the content of unreacted feed gas in the effluent gas.

21. An apparatus according to claim 18 wherein the gas analyzer determines the content of byproduct gas in the effluent gas.

22. An apparatus according to claim 18 that controls the rate of introduction of feed gas from the result of the determination of the content of the effluent gas.

23. An apparatus according to claim 1 operating in batch or continuous mode.

24. An apparatus according to claim 1 which regulates the rate of stirring of the mixture of liquid medium and feed gas.

* * * * *